United States Patent [19]

Miller

[11] Patent Number: 4,753,758
[45] Date of Patent: Jun. 28, 1988

[54] RESPIRATORY HUMIDIFIER

[75] Inventor: Kenneth G. Miller, Corona Del Mar, Calif.

[73] Assignee: Intertech Resources Inc., Bannockburn, Ill.

[21] Appl. No.: 34,287

[22] Filed: Apr. 2, 1987

Related U.S. Application Data

[60] Continuation-in-part of Ser. No. 719,886, Apr. 3, 1985, Pat. No. 4,657,713, which is a division of Ser. No. 496,103, May 19, 1983, Pat. No. 4,532,088.

[51] Int. Cl.$^4$ .................... A61M 16/18; B01F 3/04
[52] U.S. Cl. ......................... 261/139; 128/203.17; 128/203.27; 219/275; 219/276; 219/362; 261/142; 261/156; 261/DIG. 65
[58] Field of Search ............... 261/104, 107, 66, 71, 261/4–6, 138, 139, 142, 154, 156, DIG. 17, DIG. 65; 210/175, 180, 181, 184; 128/203.16, 203.17, 203.26, 203.27, 204.17; 55/259; 219/271–276, 362; 122/28

[56] References Cited

U.S. PATENT DOCUMENTS

| | | | |
|---|---|---|---|
| 649,521 | 5/1900 | Libbey | 128/203.26 |
| 3,234,357 | 2/1966 | Seuthe | 261/142 X |
| 3,659,604 | 5/1972 | Melville et al. | 128/203.27 |
| 3,757,082 | 9/1973 | Goicoechea | 261/DIG. 65 |
| 3,864,440 | 2/1975 | Giocoechea | 261/DIG. 65 |
| 3,954,920 | 5/1976 | Heath | 261/DIG. 65 |
| 3,982,095 | 9/1976 | Robinson | 261/DIG. 65 |
| 4,051,205 | 9/1977 | Grant | 261/DIG. 65 |
| 4,101,294 | 7/1978 | Kimura | 261/104 X |
| 4,203,027 | 5/1980 | O'Hare et al. | 128/203.27 X |
| 4,216,176 | 8/1980 | Tanaka | 261/154 X |

Primary Examiner—Richard L. Chiesa
Attorney, Agent, or Firm—Marshall, O'Toole, Gerstein, Murray & Bicknell

[57] ABSTRACT

A humidifier assembly is disclosed. The humidifier assembly includes a housing, a heater in the housing, a hollow shell on the housing, a partition wall within the shell, and a liquid water inlet that is unitary with the hollow shell. The heater provides an exposed heated surface for contacting liquid water in a direct heat transfer relationship. The hollow shell and the partition wall together define a humidification chamber. The hollow shell also defines a breathable gas inlet and a humidified, breathable gas outlet, both of which communicate with the humidification chamber. The partition wall includes a hydrophobic filter that permits water vapor but not liquid water to pass therethrough. The hollow shell, the partition, wall and the housing together define a liquid water-tight but water vapor permeable water reservoir between the partition wall and the heater. The liquid water inlet comunicates directly with the water reservoir and provides liquid water that can be vaporized upon contact with the heated surface. Vaporized water passes through the hydrophobic filter into the humidification chamber to humidify the breathable gas.

16 Claims, 3 Drawing Sheets

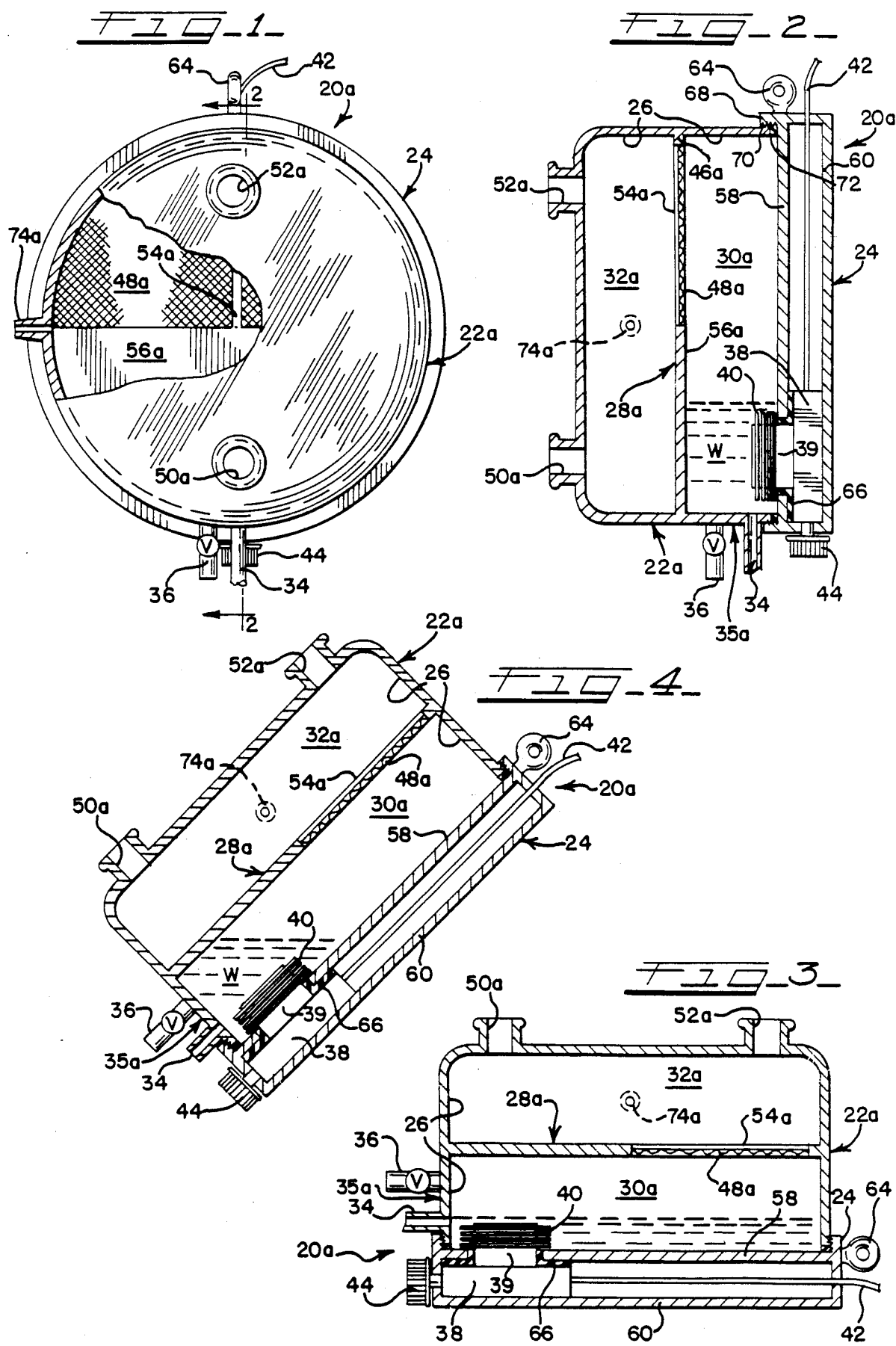

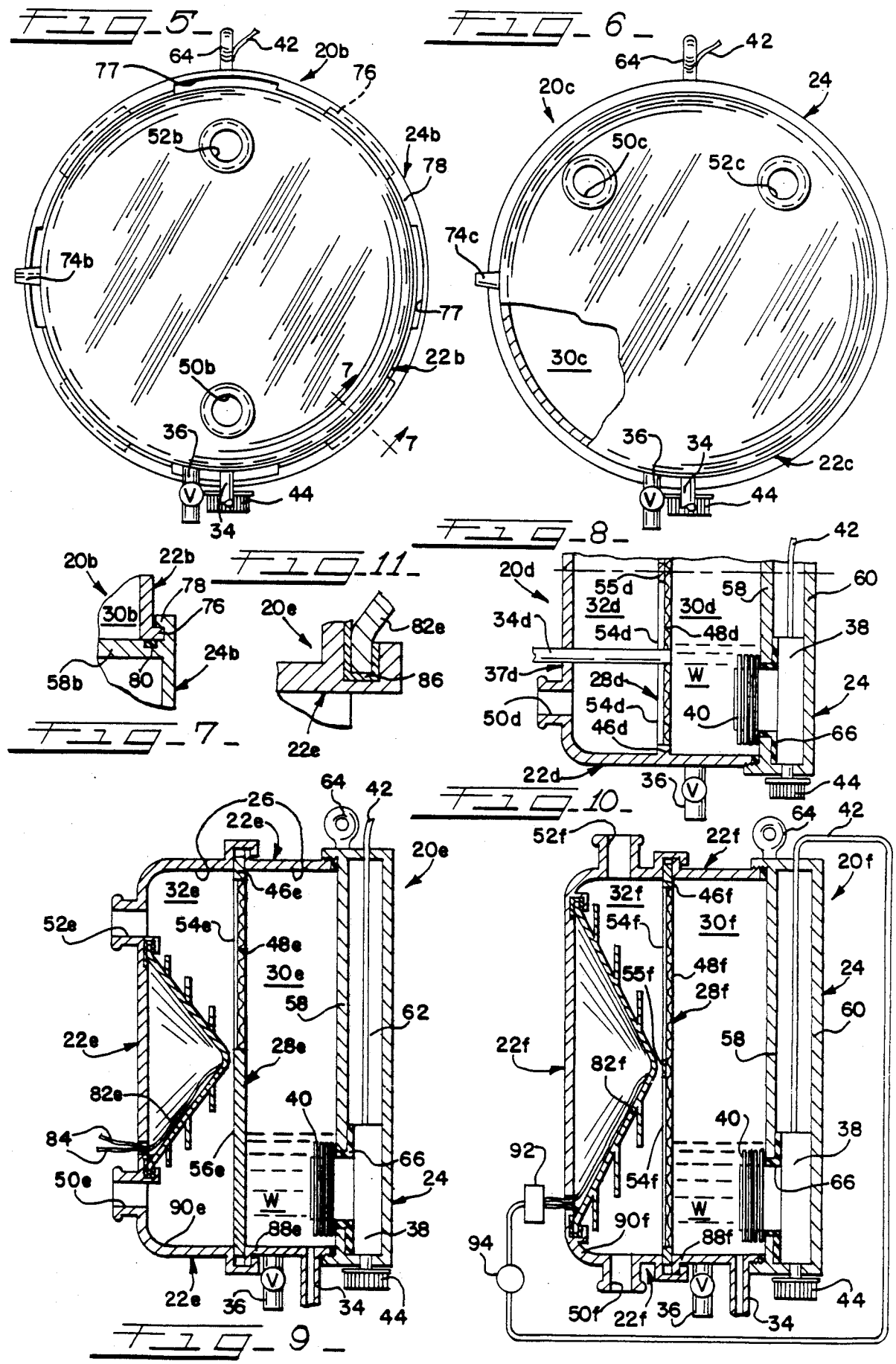

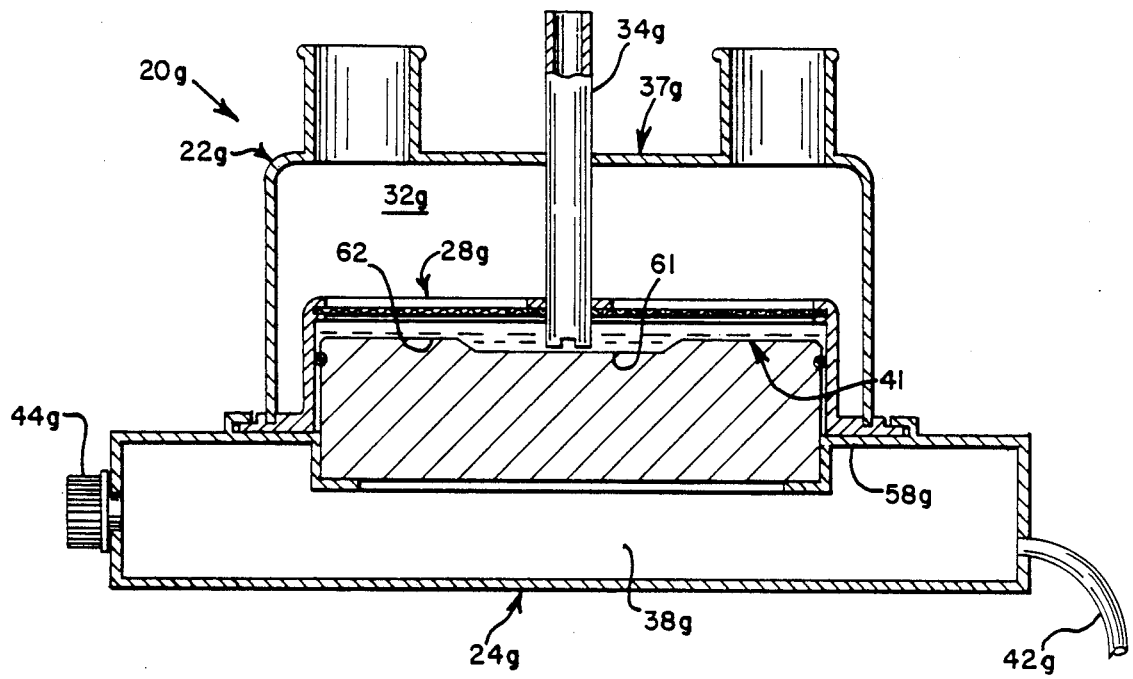
FIG_12_
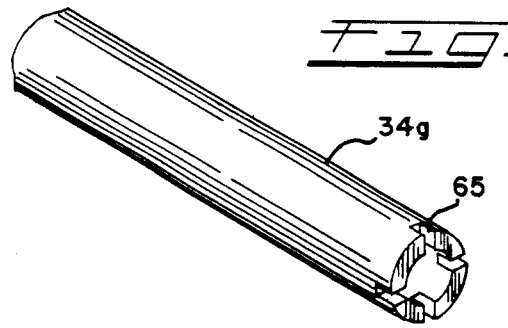
FIG_13_

RESPIRATORY HUMIDIFIER

REFERENCE TO RELATED APPLICATIONS

This patent application is a continuation-in-part application of U.S. patent application Ser. No. 719,886 filed on Apr. 3, 1985, now U.S. Pat. No. 4,657,713, which in turn is a division of Ser. No. 496,103 filed July 19, 1983, now U.S. Pat. No. 4,532,088.

TECHNICAL FIELD OF THE INVENTION

The present invention is broadly directed to a respiratory humidifier and generally relates to the field of inhalation therapy. In particular, the present invention is directed to a humidifier assembly for humidifying a breathable, oxygen-containing gas or vapor before such is administered to a patient.

BACKGROUND OF THE INVENTION

Inhalation therapy is the medical art of treating a patient with a breathable gas (such as air, oxygen or a mixture of air and oxygen) which may or may not contain medication.

The prior art is replete with a variety of different types of inhalation-therapy devices. Some types of inhalation-therapy devices operate by combining water vapor with a humidifiable breathable gas, while other types operate by combining fine liquid water droplets (or mist) with such a gas. Yet other types of these devices operate by bubbling a humidifiable breathable gas through water, or by heating the water, to generate water vapor which is later combined with a humidifiable breathable gas.

For example, each of U.S. Pat. Nos. 4,216,176 (to Tanaka); 4,110,419 (to Miller); 3,954,920 (to Heath); 3,820,540 (to Hirtz et al.); and 1,732,674 (to Dever), discloses an air-humidifier device employing either radiant-heating means and/or convection-heating means to evaporate water from a wetted wick or the like to thereby humidify air passing therethrough, while in each of U.S. Pat. Nos. 3,982,095 (to Robinson); and 3,864,440 (to Giocoechea), air is bubbled through a heated body of water for air humidification purposes.

U.S. Pat. No. 3,809,374 to Schossow employs both conduction-heating means and convection-heating means to humidify air. Briefly, Schossow discloses a vaporizer-humidifier wherein an electrical heater is immersed into a body of water to produce water vapor. The Schossow patent teaches using mechanical mixing means to mix the thus generated water vapor with air.

One problem with inhalation-therapy devices of the various types mentioned above (except perhaps for the '540 patent to Hirtz et al.) is that each device is operative generally in only one position (i.e. only when disposed vertically or only when positioned on a horizontal surface) and will not operate when positioned on its side. The '540 device, however, poses other problems in that it requires periodic disassembly to re-wet its porous water-storage element.

A problem which arises when employing the gas-bubbler types of inhalation-therapy devices is that the bubbling of a gas through a body of water requires pressurization of the gas to overcome an inherent pressure differential presented by the body of water. Moreover, bubbler devices generally do not effectively use all water contained therewithin. Also, the rate at which heat is transferred into the body of water for water-vaporization purposes is generally inefficient and slow.

The inhalation-therapy art also includes water mist-producing devices. For example, each of U.S. Pat. Nos. 4,101,611 (to Williams); and 3,864,544 (to van Amerongen), discloses a device wherein water is first heated, then nebulized, and finally mixed with a gas that is to be humidified. Each of U.S. Pat Nos. 4,116,387 (to Kremer et al.); and 3,771,721 (to van Amerongen), however, excludes the water-heating step prior to water nebulization.

One problem experienced when a liquid water particle is introduced into an air stream for purposes of humidifying the air, of course, is the cooling effect experienced when the sensible heat of the air provides the latent heat necessary to evaporate each water particle. The humidified air may in fact be too cold for many inhalation-therapy applications.

While some of the above-discussed inhalation-therapy devices are large and cumbersome, others may operate in a complicated manner involving cooperation of a variety of mechanical, electrical, and/or electromechanical elements.

Yet another problem met when the various types of water vapor-producing and/or gas bubbler-based devices discussed above are used in connection with inhalation therapy is that it is often necessary to use sterile water in the inhalation therapy device. Use of sterile water, currently costing as much as several dollars a quart, thus becomes an economic consideration. It would be desirable to be able to use a less costly form of relatively clean water for purposes of inhalation therapy.

The humidifier assembly of the present invention minimizes the drawbacks of the aforementioned prior art humidifiers and provides an apparatus that is reliable and relatively inexpensive to use.

SUMMARY OF THE INVENTION

The humidifier assembly of the present invention provides an economical apparatus that can operate effectively when in the vertical position, the horizontal position, or any position therebetween. This feature is of importance in hospital applications where it is necessary to position a humidifier assembly alongside a patient utilizing any space or support structure that may be available in any given instance.

The humidifier assembly of the present invention includes a housing, a heater in the housing, a hollow shell on the housing, a partition wall within the shell, and a liquid water supply into the hollow shell. The heater provides an exposed heated surface that allows liquid water to contact the heater in a direct heat transfer relationship. The hollow shell together with the partition wall define a humidification chamber. The hollow shell also defines a breathable gas inlet and a humidified, breathable gas outlet, both of which communicate with the humidification chamber.

The partition wall includes a hydrophobic filter that permits water vapor, but not liquid water, to pass through the filter. The hollow shell, the partition wall and the housing together define a liquid water-tight but water vapor-permeable reservoir for the liquid water. The water reservoir is located between the partition wall and the exposed heated surface of the heater.

The liquid water supply communicates directly with the water reservoir and provides liquid water that can be vaporized upon contact with the heated surface. The vaporized water, in turn, passes through the hydrophobic filter into the humidification chamber for humidifying the breathable gas.

BRIEF DISCUSSION OF THE DRAWINGS

FIG. 1 is a partially cut-away plan view of the humidifier assembly of the present invention mounted vertically;

FIG. 2 is a sectional view of the FIG. 1 embodiment, taken generally along the plane 2—2 in FIG. 1;

FIG. 3 is a sectional view of the FIG. 1 embodiment showing the present invention disposed in a horizontal position;

FIG. 4 is a sectional view of the FIG. 1 embodiment showing the present invention disposed at a position between vertical and horizontal;

FIG. 5 is a plan view of another embodiment of the humidifier assembly of the present invention;

FIG. 6 is a partially cut-away plan view of yet another embodiment of the present invention;

FIG. 7 is a fragmentary sectional view, taken along the plane 7—7 in FIG. 5 and on an enlarged scale relative thereto;

FIG. 8 is a partially fragmented sectional view of still another embodiment of the present invention;

FIG. 9 is a sectional view of yet another embodiment of the present invention;

FIG. 10 is a sectional view of still another embodiment of the present invention;

FIG. 11 is a fragmentary sectional view, on an enlarged scale relative to FIG. 9 and illustrating a detail shown therein;

FIG. 12 is a partially cut-away sectional view of yet another embodiment of the humidifier assembly of the present invention; and FIG. 13 is a perspective view of a liquid water supply, shown in FIG. 12, on an enlarged scale relative to FIG. 12.

Because of the many embodiments of the present invention, like reference numerals refer to like component parts or elements, with a lower case letter indicating modification thereof as a result of being applied to a different embodiment.

DETAILED DESCRIPTION OF PREFERRED EMBODIMENTS

While the present invention is susceptible to embodiment in a variety of forms, there is shown in the drawings and hereinafter described in detail a number of preferred embodiments of the invention, with the understanding that the present disclosure is to be considered as an exemplification of the invention without limitation to the specific embodiments illustrated.

Referring to FIGS. 1–4, one embodiment of a humidifier assembly 20a for humidifying a breathable vapor is shown. Another embodiment of the humidifier assembly 20b is shown as FIGS. 5 and 7. Yet another embodiment of the humidifier assembly 20c is shown in FIG. 6. Still another embodiment of the humidifier assembly 20d, which is an alternative to or a modification of the embodiment shown in FIGS. 1–4, is shown in FIG. 8. A further embodiment of the humidifer assembly 20e of the present invention, showing inclusion of a second heating means, is shown in FIGS. 9 and 11. FIG. 10 shows a humidifier assembly 20f which is an alternative to or a modification of the FIG. 9 embodiment. Yet another embodiment of the humidifier assembly 20g is shown in FIG. 12.

In general, the humidifier assembly of this invention comprises a housing, a heater in the housing, and a hollow shell or canister on the housing. In particular, the hollow shell or canister is mounted on the housing in a liquid-tight manner. A partition wall, at least in part permeable to water vapor but impermeable to liquid water, is disposed within the hollow shell. The partition wall together with the shell define a humidification chamber. The housing, the partition wall and the shell together define a water reservoir. The heater is positioned in the housing in a manner so as to provide a heated surface in a direct heat transfer relationship to water present in the water reservoir. The water vapor-permeable portion of the partition wall includes a hydrophobic filter.

The hollow shell also defines an inlet and an outlet to the humidification chamber for a breathable gas. The hollow shell may optionally define or be provided with a liquid inlet that communicates with the water reservoir, or a drain for draining liquid water from the reservoir, or both.

Another feature of the present invention, which is an insert for the humidification chamber, provides the humidifier assembly with a means for modulating the overall compliance of the humidification system.

Referring initially to FIGS. 1 and 2, the humidifier assembly 20a comprises a canister or shell 22a removably mounted on a housing 24. The shell 22a defines a hollow shell cavity 26 (FIGS. 2-4). A partition wall 28a, disposed within shell 22a, divides the shell cavity 26 into a humidification chamber 32a and a water reservoir 30a. Humidification chamber 32a, thus, is defined by shell 22a and partition wall 28a. Water reservoir 30a is defined, in turn, by shell 22a, partition wall 28a, and a sidewall 58 of housing 24. It is to be understood that the spacing between the partition wall and the housing sidewall has been exaggerated in the embodiments shown in FIGS. 2-4 and 8-10, for the purpose of identifying and discussing selected components or features of the present invention, and that the actual spacing is less than is shown in these embodiments.

The shell 22a is also provided with a water inlet means 34, communicating with reservoir 30a, for introducing liquid water W into reservoir 30a. Optionally, shell 22a can also be provided with a drain means 36 for draining liquid water from reservoir 30a. Drain means 36 may be provided with a valve, or it can be closed off with a removable plug, if desired. Drain means 36, if present, is preferably arranged at the lowermost portion of shell 22a, when the humidifier assembly 20a is disposed in its normal use position, to provide effective drainage.

The water inlet means 34 can be molded as part of the shell 22a and thus can be unitary with the shell (FIGS. 1-4). Preferably, the water inlet means 34 is positioned on the shell or canister 22a so as to supply liquid water into water reservoir 30a below the normal liquid level of the liquid water W that is in reservoir 30a. Water inlet means 34 can be situated on the skirt portion 35a of shell or canister 22a as shown in FIGS. 2-4, or it can be situated on the crown portion 37d of shell 22d and pass through the humidification chamber 32d, as is shown in FIG. 8 in reference to the modified water-inlet means 34d.

The humidifier assembly of the present invention further comprises a controllable heating means 38 mounted in housing 24 (FIGS. 2-4). The heating means 38g (FIG. 12) can include a heated surface 41 that is substantially coplanar with sidewall 58g, or that is configured as a plug type protuberance 39 extending into water reservoir 30a (FIGS. 2-4). Protuberance 39 can be provided with heat transfer fins 40, if desired.

Heat input into liquid water W contained in reservoir 30a produces water vapor which passes through a portion of partition wall 28a and is commingled with the breathable gas in humidification chamber 32a as will be described in greater detail hereinbelow. Heating means 38 is electrically connected by a cable 42 to a suitable power source 94 (e.g. as is shown in FIG. 10). A knurled knob 44 on heating means 38 is operably associated with a control device, e.g. a rheostat (not shown), for controlling the flux of heat into the body of water W contained within reservoir 30a.

The partition wall 28a divides the shell cavity 26 into the two above-mentioned chambers 30a and 32a, i.e. and the water reservoir 30a and the humidification chamber 32a. At least a portion of the partition wall 28a is adapted to allow water vapor to pass from reservoir 30a into humidification chamber 32a. The partition wall 28a can include an annular ring or collar 46a, which can be unitary with the shell 22a as shown in FIGS. 2-4, although in other embodiments of the present invention (e.g. FIGS. 9 and 10) the collar 46e and shell 22e need not be unitary. Such a ring or collar serves as a support for a hydrophobic filter element which permits only water vapor to pass therethrough. A filter element 48a suitable for this purpose is affixed to a portion of the circumferential boundary of collar 46a (FIGS. 2-4).

Preferably, the filter element 48a comprises a commercially available generally hydrophobic filter means of the type which can also filter out undesirable mircroorganisms. Water-vapor permeable membranes which do not allow liquid water to pass therethrough but which do allow water vapor to do so are well known in the art. See, e.g., U.S. Pat. No. 3,912,795 (to Jackson). Commercially available filter materials suitable for use in the present invention may have a pore size of about 0.2 to 0.5 microns. The pore size can be smaller or larger as desired, however, depending upon the potential contaminents that are to be excluded from the humidification chamber and the water-vapor flow-through rate that is desired for the filter. Particularly preferred filter materials for use in accordance with the principles of the present invention are microporous expanded polytetrafluoroethylene (PTFE) structures having a matrix of nodules interconnected with fibrils. Alternatively, membrane filters that are inherently hydrophobic or fibrous mats treated with a water-repellant substance can also be used. The degree of porosity of the filter material can be selected to meet the contemplated throughput requirements mentioned above.

Thus, one feature or advantage of the humidifier assembly of the present invention is that the presence of the filter element 48a does not require using sterile water because the pore size of the filter element can readily be selected to exclude contaminents such as bacteria, mold spores, etc. from the humidification chamber. Accordingly, distilled water, bottled water or even tap water may be used.

The partition wall 28a includes at least one radially disposed rib 54a (FIG. 1) to provide support for filter element 48a (FIG. 2). It is further contemplated that upstanding rib 54d can be unitary with collar 46d, and that a transverse rib 55d can be unitary with upstanding rib 54d, as is shown in FIG. 8. In particular, filter element 48d can be affixed to each of collar 46d, vertical rib 54d and transverse rib 55d, all of which provide filter element 48d with a somewhat rigid quality. A similar arrangement is shown in FIG. 10, except that in this embodiment collar 46f is not unitary with shell 22f.

A portion of the partition wall 28a can be provided with a retaining wall 56a as is shown in FIG. 1. Retaining wall 56a can be unitary with each of the canister or shell 22a and the rib 54a to provide a liquid barrier between reservoir 30a and humidification chamber 32a when the humidifier assembly 20a is disposed in the vertical position (FIG. 2) should the filter element 48a fail. In one of the other embodiments, partition wall 28e is shown including such a retaining wall 56e (FIG. 9).

In yet another embodiment of the present invention a modification of the partition wall 28d is shown (FIG. 8). That is, the liquid water W is retained within water reservoir 30d by the filter element 48d itself. Further, as shown in the FIG. 8 embodiment, partition wall 28d can be unitary with shell 22d via the annular collar 46d. The FIG. 8 embodiment also shows that the partition wall 28d can be adapted to have, the water inlet means 34d pass through partition wall 28d, to provide liquid water into fluid reservoir 30d, while partition wall 28d maintains its liquid-tight character to retain liquid water W in fluid reservoir 30d.

The shell further defines a breathable vapor inlet 50a and a humidified, breathable vapor outlet 52a, each communicating with the humidification chamber 32a (FIGS. 1 and 2). The inlet 50a and the outlet 52a permit a breathable, oxygen-containing gas to pass through humidification chamber 32a while the gas is being humidified. Another arrangement of inlet 50c and outlet 52c on shell 22c is shown in FIG. 6. Yet another arrangement of inlet 50f and outlet 52f on shell 22f is shown in FIG. 10.

In accordance with other features of the present invention, housing 24 can be provided with a fluid leak-proof sleeve 66 (FIG. 2) disposed between heating means 38 and housing sidewall 58. A suitable sleeve material for this purpose is made of PTFE because PTFE not only provides the water reservoir 30a with a fluid leak-proof seal but also functions as an insulating material to reduce the rate of heat transfer from heating means 38 into sidewall 58. The housing 24 can also be provided with an eye 64 (FIG. 2) to allow hanging the humidifier assembly 20a from structure (not shown) if desired. The housing 24 is further provided with an exterior wall 60 (FIG. 2), spaced from sidewall 58, which functions as a base for the humidifier assembly 20a when it is disposed on its side, i.e. horizontally, as shown in FIG. 3.

Yet another feature of the present invention is that the humidifier assembly 20a can be adapted to provide a preselected manner of vaporizing of the body of water W contained within fluid reservoir 30a, whether disposed in the vertical position (FIG. 2), the horizontal position (FIG. 3), or any position therebetween (FIG. 4). One such manner of, or method for, vaporizing water W contemplates causing nucleation boiling.

The finned, heat-transfer surface 40 of heating means 38 can be adapted, e.g. to include surface rugosities, to cause minute bubbles to form along the fins thereof, such bubbles tending to detach from the finned, heat-transfer surface 40 when still relatively minute in size. Nucleation boiling of the water W thus provides relatively rapid heat-up of the humidifying water, which is desirable in a number of applications.

Alternatively, the heated surface 41 of heating means 38g can be adapted to provide relatively rapid heat-up of the water W within the water reservoir substantially without bubble formation. For example, the cross sectional area provided by heated surface 41 can be sufficiently large, in relation to the cross sectional area of the water reservoir, to enable the heated surface 41 to serve as the floor of the water reservoir, as is shown in FIG. 12. Further, the heated surface 41 can be adapted to include a central surface depression 61 and an annular surface 62 positioned above depression 61 when humidifier assembly 20g is disposed horizontally as shown. The humidifier assembly 20g can also have its liquid water inlet means 34g disposed through the crown 37g of shell 22g, through humidification chamber 32g, and through partition wall 28g. Liquid water inlet means 34g can thus be arranged to communicate with the water W in the water reservoir, and can be further adapted to have its outlet end substantially centered relative to the surface depression 61 and in close proximity thereto. The outlet end of liquid water inlet means 34g can further be provided with a plurality of circumferentially-spaced radially-disposed slots or fluid passageways 65 (FIG. 13) to cause water introduced into the reservoir to be substantially equally distributed over the area of heated surface 41 and in close proximity thereto. Such an arrangement facilitates relatively rapid heat-up of water being introduced into the water reservoir.

Preferably, the amount of water W in the water reservoir displaces about 30 to about 50 percent of the total available volume within the water reservoir and the water vapor displaces the remainder. Methods or systems for maintaining liquid level in water reservoirs are well known in the art. See, e.g., U.S. Pat. Nos. 3,809,374 (to Schossow); and 4,110,419 (to Miller). Accordingly, the humidifier assembly of the present invention can readily be interconnected with a suitable fluid delivery system (not shown) to maintain a predetermined liquid water level within the water reservoir.

As yet another feature or advantage of the present invention, the shell 22a can include a drain or vent 74a (FIG. 1) to substantially lessen the likelihood of liquid water being carried along with the humidified breathable gas, as such exits humidification chamber 32a via outlet 52a, in the event that the filter element and the humidification fluid liquid-level delivery system (not shown) both fail.

One manner or method of affixing the shell and the housing 24 together contemplates using threaded connections. For example, housing 24 can include an internally threaded circumferential portion 68 and shell 22a can include circumferential threads 70 meshably engagable with the inner circumferential threads of housing 24 (FIG. 2). A fluid leak-proof seal 72 can be disposed between shell 22a and housing sidewall 58. A fluid leak-proof seal that is suitable for this purpose can be a commercially-available O-ring (e.g. of silicone rubber) or can be a ring or annulus of PTFE.

Another method or manner of affixing the shell and the housing together contemplates providing the shell 22b with a plurality of circumferentially-spaced radially-disposed flanges or ears 76 (FIGS. 5 and 7). In particular, the housing 24b can accordingly include a like plurality of peripherally-spaced radially-formed slots or grooves 77 (FIG. 5) adapted to receive the flanges or ears 76. The housing 24b can further include a like plurality of circumferentially-spaced radially-disposed flanged retaining means 78 (FIGS. 5 and 7), each of which is slidably engagable with a respective one of the ears 76, to provide shell 22b and housing 24b with a bayonet-type of closure when either of the shell 22b or the housing 24b is rotated one-quarter turn relative to the other. Further, sidewall 58b of housing 24b can be slotted (FIG. 7) to receive an annular, fluid leak-proof seal or gasket 80, for providing a fluid leak-proof seal or seat between shell 22b and housing 24b. A suitable seal or gasket for this purpose can be an elastomeric O-ring (e.g. silicone rubber) or an annulus or ring or PTFE.

Reference is next invited to FIGS. 9 and 10 where yet another advantage or feature of the present invention is shown. In certain situations it is desirable to be able to modulate the compliance of the humidification system. Such a humidification system typically can comprise the humidifier assembly (disclosed herein), suitable conduit (not shown) attached to the breathable gas inlet 50a to supply a breathable gas that is to be humidified to the humidification chamber 22a, and suitable conduit (not shown) attached to outlet 52a to supply the humidified, breathable gas to a patient. Modulation of the humidification system contemplates absolute humidity and temperature of the humidified gas being supplied to the patient.

To this end, the humidifier assembly 20e can be provided with a baffled, conical heating means 82e, rotatably and removably engagable with shell 22e (such as by the quarter-turn twist arrangement discussed above in connection with FIG. 5). Conical heating means 82e can be disposed within humidification chamber 32e and spaced from partition wall 28e, as shown in FIG. 9. The canister or shell 22e (FIG. 9) can be of separable, two part construction. In particular, shell 22e can include a fluid reservoir portion 88e defining the water reservoir 30e, and a portion 90e defining the humidification chamber 32e. Shell 22f (FIG. 10), also of two-part construction, can similarly include separable fluid reservoir and gas humidification portions 88f and 90f.

Conical heating means 82e, separable from shell 22e, not only displaces volume within the humidification chamber 32e but also heats the humidified breathable gas (that passes through the humidification chamber) before such gas is supplied to the patient, to enable monitoring the compliance of the humidification system. Conical heating means 82e can be a resistance-type heater, connected by wires 84 to a suitable power source (not shown). Conical heating means 82e can accordingly be constructed from a suitable, heatable, commercially-available electrically-conductive polymer, if desired. An alternative embodiment of the removable, conical heating means 82f is shown in FIG. 10. The alternative or modified conical heating means 82f has a broader base and displaces more volume than the conical heating means 82e shown in FIG. 9. Each conical heating means embodiment 82e and 82f is removably mounted within the humidifcation portion 90e and 90f of its respective shell by bayonet-mounting structure provided on the conical heater and shell. It is contemplated that either one of the removable, conical heating means 82e or 82f can be replaced by modified heating means (not shown) having the same size base but a different depth or altitude to change the amount of volume displacement within the humidification chamber. Each heating means 82e and 82f can be appropriately spaced from its respective partition wall 28e and 28f to reduce the likelihood of heat damage thereto.

To accommodate a conical heating means that is wide-based in relation to its shell, such as heating means 82f, it is contemplated that shell 22f can be adapted to have gas inlet 50f and gas outlet 52f both vertically arranged as shown in FIG. 10. Alternatively, for a narrower-based heating means, such as conical heating means 82e, it is contemplated that shell 22e can have its inlet 50e and outlet 52e arranged closer together as is shown in FIG. 9.

Preferably, insulation 86 is provided between the shell 22e and the removable, conical heating means 82e, as is shown in FIG. 11. The presence of insulation 86 thus can substantially lessen the likelihood of heat damage to shell 82e by heater 82e. The shell or canister can furthermore be made of a suitable, commercially-available heat-resistant material, adapted to accommodate a predetermined amount of localized heating such as is caused by heater 82e without damage to the shell.

It is further contemplated that the fluid reservoir and gas humidification portions 88e and 90e of shell 22e can be removably held together by bayonet-mounting structure which not only enables the two shell portions to be snugly yet removably held together but also enables the partition wall 28e to be firmly held therebetween (FIG. 9). A similar arrangement is presented in the FIG. 10 embodiment. In particular, referring to shell 22e (FIG. 9), to disassemble shell 22e, either one of the fluid-reservoir and gas-humidification portions 88e and 90e is rotated relative to the other. Once shell 22e is disassembled (i.e. gas humidification portion 90e separated from fluid reservoir portion 88e), partition wall 28e can be separated from gas humidification portion 90e enabling removal of the conical heater means 82e from shell 22e.

It is also contemplated that the removable partition wall 28e can have a collar 46e that provides a fluid-tight seal between the fluid-reservoir and gas-humidification portions 88e and 90e. The FIG. 10 embodiment can provide a similar fluid-tight seal.

The humidifier assembly of the present invention can also be equipped with a temperature-control means 92 (FIG. 10) for automatically controlling the heat flux passed into the humidification chamber 32f by conical heating means 82f if desired. The FIG. 9 embodiment can include a like arrangement. Temperature control of respiratory humidifiers is well known in the art. See, e.g., U.S. Pat. Nos. 3,820,540 (to Hirtz et al.); 3,864,544 (to van Amerongen); and 4,110,419 (to Miller).

What has been illustrated and described herein is a novel respiratory humidifier assembly for humidifying a breathable gas or vapor. While the humidifier assembly of the present invention has been illustrated and described with reference to a number of preferred embodiments, the present invention is not limited thereto. On the contrary, alternatives, changes or modifications may become apparent to those skilled in the art upon reading the foregoing description. For example, the shell can be made of a transparent, high-impact plastic commercially available at a relative low cost. Moreover, a variety of shell or canister designs, including obvious modifications of the shell design disclosed herein, can be manufactured to provide the humidifier assembly of the present invention with a wide assortment of replacement parts to maintain sterility of specific humidifier assembly component parts, or to affect modulation of the compliance of the humidification system, whichever is desired. Accordingly, such alternatives, changes and modifications are to be considered as forming a part of invention insofar as they fall within the spirit and scope of the appended claims.

I claim:

1. A humidifier assembly for humidifying a breathable gas, comprising:
   a heater housing;
   heater means mounted on said heater housing, said heater means having an exposed heated surface for contacting liquid water in a direct heat transfer relationship therewith;
   a hollow shell, means on said shell and on said heater housing for removably fastening said shell to said housing, said housing including an inlet for breathable gas and an outlet for humidified breathable gas;
   a partition wall means at least partially formed by a hydrophobic filter means, in the hollow shell and defining together with the shell a humidification chamber that communicates with said gas inlet and said gas outlet, said filter means being positioned for passing water vapor into the breathable gas, and the partition wall together with said hollow shell and said housing defining a water-tight but water-vapor permeable liquid water reservoir between said filter means and said heated surface; and
   liquid water supply means connected to said hollow shell and communicating directly with said water-tight reservoir;
   said liquid water supply means providing liquid water in the water-tight reservoir and partially filling said reservoir and covering said heated surface, said heated surface converting a portion of said liquid water to water vapor, and a part of said reservoir above said liquid water receiving said water vapor, and said water vapor passing from the water-tight reservoir through said filter means and into said humidification chamber.

2. The humidifier assembly of claim 1, and further comprising a water drain means on said shell and communicating with said water reservoir.

3. The humidifier assembly of claim 1, wherein the humidifier assembly is included in a humidification system, the humidifier assembly further comprising a second heater means disposed within the humidification chamber to modulate compliance of the humidification system.

4. A humidifer assembly for humidifying a breathable gas, comprising
   (1) a housing wall forming an interior enclosure;
   (2) a partition wall extending across said interior enclosure and connected for support to said housing wall, said partition wall having a first portion and a second portion, said first portion being connected to said housing wall and being impermeable to liquid and vapor, said second portion being connected to said first portion and being formed by a filter which is vapor permeable;
   (3) said partition wall separating said interior enclosure into a reservoir chamber and a humidification chamber;
   (4) a heater mounted in said reservoir chamber;
   (5) a gas inlet and a gas outlet formed in said housing wall and in communication with said humidification chamber; and
   (6) liquid supply means extending through said housing wall for conducting a liquid to said reservoir chamber and filling said reservoir chamber with liquid to a level which is above said heater.

5. An assembly according to claim 4, and further including a second heater mounted in said humidification chamber.

6. An assembly according to claim 4, wherein said partition wall is removably and replaceably mounted on said housing wall.

7. An assembly according to claim 4, wherein said housing wall is formed by a heater part and a shell part, said parts being detachably connected together, said heater being mounted on said heater part, and said partition wall being mounted on said shell part.

8. An assembly according to claim 7, wherein said partition wall is removably mounted on said shell part.

9. An assembly according to claim 7, wherein said liquid supply means extends through said shell part.

10. An assembly for use with a heater housing in a humidifier, comprising a shell wall, inlet and outlet passages formed in said shell wall for flow of a breathable gas to be humidified, said shell wall having an open side, a filter wall extending across said open side and attached to said shell wall, at least a portion of said filter wall being formed by a filter which is vapor permeable, said shell wall including a rim portion and connecting means on said rim portion for removably attaching said shell wall to a housing part that includes a heater, and liquid supply means extending through said shell wall between said filter wall and said rim portion, said assembly thereby being adapted to be removably attached to the housing part that includes a heater for direct heating of the liquid.

11. An assembly according to claim 10, wherein said filter wall is removably attached to said shell wall and to said liquid supply means.

12. An assembly for humidifying a breathable gas, comprising:
  (1) a heater housing;
  (2) an electric heater mounted on one side of said housing, said heater having an exposed surface for contacting liquid water.
  (3) a cup-shaped shell having a bottom side, a gas inlet opening and a gas outlet opening formed in said bottom side, said shell further having an open interior space, an open side and a rim at said open side;
  (4) a partition wall mounted within said interior space of said shell adjacent said open side, said partition wall and said bottom side of said shell forming an enclosed humidification chamber, said partition wall including a first portion which is water vapor permeable and liquid water impermeable, and a second portion which is water vapor and liquid water impermeable;
  (5) fastening means on said heater housing and on said rim of said shell forming a sealed releasable connection between said shell and said heater housing;
  (6) said shell, said partition wall and said heater housing together forming a liquid water reservoir which encloses said heater; and
  (7) a liquid water supply inlet means connected to said shell for conducting liquid water directly into said water reservoir and partially filling said reservoir with liquid water to a level which is above said heater;
  (8) whereby in operation of the assembly the heater heats the water and forms heated water vapor in said reservoir and said heated water vapor flows through said water vapor permeable first portion of said partition wall and into said humidification chamber.

13. An assembly according to claim 12, wherein said water supply inlet means is connected to said shell between said partition wall and said rim.

14. An assembly according to claim 12, wherein said second portion of said partition wall extends to above the level of the liquid water in said water reservoir.

15. An assembly according to claim 12, and further including a second heater mounted in said humidification chamber.

16. An assembly according to claim 12, and further including means on said shell and on said partition wall for removably mounting said partition wall in said shell.

* * * * *